United States Patent
Osborne et al.

(10) Patent No.: US 10,383,888 B2
(45) Date of Patent: Aug. 20, 2019

(54) EXOPOLYSACCHARIDE FOR INFLAMMATORY DISEASE

(71) Applicant: University of Massachusetts, Boston, MA (US)

(72) Inventors: Barbara Osborne, Leverett, MA (US); Furkan Ayaz, Amherst, MA (US); Katherine Knight, Chicago, IL (US); Sara Jones, Bloomington, IN (US)

(73) Assignee: University of Massachusetts, Boston, MA (US)

( * ) Notice: Subject to any disclaimer, the term of this patent is extended or adjusted under 35 U.S.C. 154(b) by 24 days.

(21) Appl. No.: 15/095,604

(22) Filed: Apr. 11, 2016

(65) Prior Publication Data

US 2016/0317566 A1 Nov. 3, 2016

Related U.S. Application Data

(60) Provisional application No. 62/145,815, filed on Apr. 10, 2015.

(51) Int. Cl.

| | |
|---|---|
| *A61K 35/74* | (2015.01) |
| *A61P 31/04* | (2006.01) |
| *A61P 37/02* | (2006.01) |
| *C08B 37/00* | (2006.01) |
| *A61K 31/715* | (2006.01) |
| *A61K 31/736* | (2006.01) |
| *A61K 35/741* | (2015.01) |
| *A61K 35/742* | (2015.01) |
| *A61K 35/745* | (2015.01) |

(52) U.S. Cl.
CPC .......... *A61K 31/715* (2013.01); *A61K 31/736* (2013.01); *A61K 35/74* (2013.01); *A61K 35/741* (2013.01); *A61K 35/742* (2013.01); *A61K 35/745* (2013.01); *A61P 31/04* (2018.01); *A61P 37/02* (2018.01); *C08B 37/0087* (2013.01)

(58) Field of Classification Search
None
See application file for complete search history.

(56) References Cited

U.S. PATENT DOCUMENTS 9,610,307 B2 * 4/2017 Berry .................. A61K 9/0031

FOREIGN PATENT DOCUMENTS

| JP | 2011-032170 | * | 2/2011 | ............. A61K 35/74 |
| KR | 2015-025159 | * | 3/2015 | ............... C12N 1/20 |
| WO | WO2009/139655 | * | 11/2009 | |

OTHER PUBLICATIONS

Ortiz et al., "Immunology and Oxidative Stress in Multiple Sclerosis: Clinical and Basic Approach" Clinical and Developmental Immunology (2013) pp. 1-14.*
Ochoa-Reparaz et al., "The role of subcellular fractions of commensal Bacteroides fragilis in the control of experimental autoimmune encephalomyelitis" Multiple Sclerosis (2009) vol. 15: S31-S150.*
Wu et al., "Exopolysaccharide activities from probiotic bifidobacterium: Immunomodulatory effects (on J774A.1 macrophages) and antimicrobial properties" International Journal of Food Microbiology (2010) vol. 144 pp. 104-110.*
Kato et al. "Exopolysaccharide activities from probiotic bifidobacterium: Immunomodulatory effects (on J774A.1 macrophages) and antimicrobial properties" Aliment Pharmacol Ther (2004) vol. 20 pp. 1133-1141.*
Kim et al., "Oral feeding of Bifidobacterium bifidum (BGN4) prevents CD4+ CD45RBhigh T cell-mediated inflammatory bowel disease by inhibition of disordered T cell activation" Clinical Immunology (2007) vol. 123 pp. 30-39.*
Merriam-Webster's Collegiate Dictionary (1998) published by Merriam-Webster, INC, p. 924.*
Mazmanian et al., "A microbial symbiosis factor prevents intestinal inflammatory disease" Nature vol. 453 pp. 620-625 (Year: 2008).*
Ochoa-Reparaz et al., "A human commensal antigen protects against CNS demyelinating disease in mice and modulates regulatory T-cell phenotypes in humans" Multiple Sclerosis vol. 16 pp. S9-S10 (Year: 2010).*
Mao et al., "Bacteroides fragilis polysaccharide a is necessary and sufficient for acute activation of intestinal sensory neurons" Nature Communications 4:1465, pp. 1-10 (Year: 2013).*
Jones et al., "Protection from Intestinal Inflammation by Bacterial Exopolysaccharides" Journal of Immunology vol. 192 pp. 4813-4820 (Year: 2014).*
English machine translation of JP2011-032170 above, downloaded from translationportal.epo.org (Year: 2011).*
English machine translation of KR2015-025159 above, downloaded from translationportal.epo.org (Year: 2015).*
Koroleva et al., "Citrobacter rodentiunn-induced colitis: A robust model to study mucosal immune responses in the gut" Journal of Immunological Methods vol. 421 pp. 61-72 (Year: 2015).*

* cited by examiner

*Primary Examiner* — Eric Olson
(74) *Attorney, Agent, or Firm* — Schwegman Lundberg & Woessner, P.A.

(57) ABSTRACT

The invention relates to an exopolysaccharide (EPS), compositions comprising EPS and methods of use, including for treating and preventing disorders, such as inflammatory disorders.

6 Claims, 8 Drawing Sheets

EXOPOLYSACCHARIDE FOR INFLAMMATORY DISEASE

CLAIM OF PRIORITY

This application claims the benefit of priority of U.S. Provisional Patent Application No. 62/145,815, filed on 10 Apr. 2015, and is incorporated by reference herein in its entirety.

GOVERNMENT GRANT SUPPORT

This invention was made with government support under AI 098187 and DK 092054 awarded by the National Institutes of Health. The government has certain rights in the invention.

BACKGROUND OF THE INVENTION

The gastrointestinal microbiota contributes to the development and maintenance of the host immune system. The complex ecosystem of the intestinal microflora is estimated to contain over 500 different bacterial species. Some of these species are considered potentially harmful, while others are believed to be health promoting strains.

SUMMARY OF THE INVENTION

The invention relates to an exopolysaccharide (EPS), compositions comprising EPS and methods of use, including for treating and preventing disorders, such as inflammatory disorders.

One embodiment provides a method to treat or prevent an autoimmune disease comprising administering to a subject in need thereof an effective amount of a bacterial (e.g., Bacillus subtilis) exopolysaccharide as described in Example 1 so as to treat or prevent an autoimmune disease. In one embodiment, the autoimmune disease is multiple sclerosis (MS).

Another embodiment provides a method to treat or prevent inflammation comprising administering to a subject in need thereof an effective amount of a bacterial (e.g., Bacillus subtilis) exopolysaccharide as described in Example 1 so as to treat or prevent inflammation. In one embodiment, the inflammation is caused by an infectious agent. In one embodiment, the infectious agent is bacteria.

One embodiment provides a method to treat or prevent an inflammatory disease comprising administering to a subject in need thereof an effective amount of a bacterial (e.g., Bacillus subtilis) exopolysaccharide as described in Example 1 so as to treat or prevent an inflammatory disease. In one embodiment, the inflammatory disease is inflammatory bowel disease. In one embodiment, the inflammatory disease is not an intestinal disease.

In one embodiment, the bacterial strain used in the methods of the inventions is a probiotic strain.

In another embodiment, the bacterial strain used in the methods of the invention is Bacillus subtilis, Bacteroides fragilis, Bifidobacterium breve, or a combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
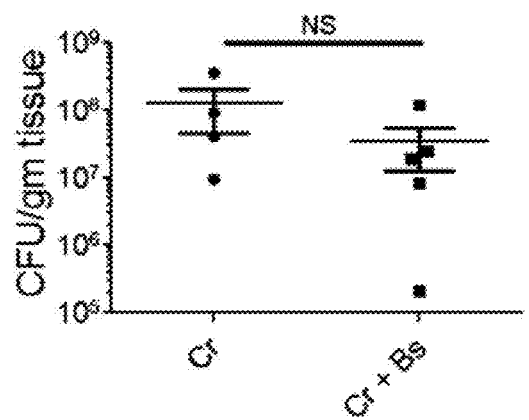
FIGS. 1A-C depict colonization and gut-induced leakiness in C. rodentium-infected mice after treatment with B. subtilis. Mucosal (A) and lumenal (B) colonization of C. rodentium 11 dpi. FITC-dextran in serum of mice 11 dpi with lux$^+$ C. rodentium (C). Cr, C. rodentium-infected mice; Cr+Bs, mice treated with B. subtilis 24 h prior to C. rodentium. The results are averages from two independent experiments, and a total of five to six mice were assessed for each group. NS, No statistical difference.

Disclosed herein is the discovery that purified exopolysaccharide (EPS) from *Bacillus subtilis* provides protection from several inflammatory diseases. Further disclosed is that EPS pretreatment protects subjects from multiple sclerosis (MS) (as demonstrated with a murine model for multiple sclerosis known as EAE). Subjects that received EPS prior to induction of disease were completely protected from the disease, while subjects that received EPS at the time of disease induction displayed partial protection. Thus, EPS find use in preventing MS and treating recurrent relapses in MS.

For the purposes of clarity and a concise description, features can be described herein as part of the same or separate embodiments; however it will be appreciated that the scope of the invention may include embodiments having combinations of all or some of the features described.

The terminology used herein is for the purpose of describing particular embodiments only and is not intended to be limiting of the invention.

As used herein, the indefinite articles "a", "an" and "the" should be understood to include plural reference unless the context clearly indicates otherwise.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "about" means plus or minus 10% of the indicated value. For example, about 100 means from 90 to 110.

As used herein, the term "subject" refers to any animal (e.g., mammals, birds, reptiles, amphibians, fish), including, but not limited to, humans, non-human primates, rodents, and the like, which is to be the recipient of a particular treatment. Typically, the terms "subject" and "patient" may be used interchangeably herein in reference to a subject.

As used herein, the term "administering" refers to providing a therapeutically effective amount of a chemical or biological compound (e.g., EPS) or pharmaceutical composition to a subject. The chemical or biological compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; ear drops; sprays, including nasal sprays; other proteins and peptides; synthetic polymers; microspheres; nanoparticles; and the like.

The chemical or biological compound or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Moreover, the packaging material may be biologically inert or lack bioactivity, such as plastic polymers, silicone, etc. and may be processed internally by the subject without affecting the effectiveness of the agent packaged and/or delivered therewith.

The term "effective amount," as applied to the compound(s), biologics and pharmaceutical compositions described herein, means the quantity necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound, biologic or pharmaceutical composition used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and like factors well known to one of skill in the relevant scientific art. Some variation in dosage can occur depending upon the condition of the subject being treated, and the physician or other individual administering treatment will, in any event, determine the appropriate dose for an individual patient.

As used herein, "disorder" refers to a disorder, disease or condition, or other departure from healthy or normal biological activity, and the terms can be used interchangeably. The terms would refer to any condition that impairs normal function. The condition may be caused by sporadic or heritable genetic abnormalities. The condition may also be caused by non-genetic abnormalities. The condition may also be caused by injuries to a subject from environmental factors, such as, but not limited to, cutting, crushing, burning, piercing, stretching, shearing, injecting, or otherwise modifying a subject's cell(s), tissue(s), organ(s), system(s), or the like.

As used herein, "treatment" or "treating" refers to arresting or inhibiting, or attempting to arrest or inhibit, the development or progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms. Additionally, treatment can be applied to a subject or to a cell culture.

Exopolysaccharides

Exopolysaccharides are high-molecular-weight polymers that are composed of sugar residues and are secreted by a microorganism into the surrounding environment. Microorganisms synthesize a wide spectrum of multifunctional polysaccharides including intracellular polysaccharides, structural polysaccharides and extracellular polysaccharides or exopolysaccharides (EPS). Exopolysaccharides generally consist of monosaccharides and some non-carbohydrate substituents (such as acetate, pyruvate, succinate, and phosphate). Owing to the wide diversity in composition, exopolysaccharides have found multifarious applications in various food and pharmaceutical industries.

Inflammatory Disorders

One embodiment provided herein is a method to prevent or treat inflammation induced by infectious agents, and other inflammatory processes such as those that result in inflammatory bowel diseases comprising administering to a subject in need thereof exopolysaccharides from *Bacillus subtilis*.

Inflammatory disorders are a group of disorders that underlie a variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. Examples of disorders associated with inflammation include, but are not limited to: Acne vulgaris; Asthma; Autoimmune diseases (including Crohn's and lupus); Autoinflammatory diseases; Celiac disease; Chronic prostatitis; Glomerulonephritis; graft vs host disease; Hypersensitivities; Inflammatory bowel diseases; Pelvic inflammatory disease; Reperfusion injury; Rheumatoid arthritis; Sarcoidosis; Sepsis; Transplant rejection; Vasculitis or Interstitial cystitis.

Inflammation can be caused by an infectious agent and/or organism or response thereto. Infection is the invasion of a host organism's body tissues by disease-causing agents, their multiplication, and the reaction of host tissues to these organisms and the toxins they produce. Infectious diseases, also known as transmissible diseases or communicable diseases, comprise clinically evident illness (i.e., characteristic medical signs and/or symptoms of disease) resulting from the infection, presence and growth of pathogenic biological agents in an individual host organism. Infections are caused by infectious agents such as viruses, viroids, and prions, microorganisms such as bacteria, nematodes such as roundworms and pinworms, arthropods such as ticks, mites, fleas, and lice, fungi such as ringworm, and other macroparasites such as tapeworms. Hosts can fight infections using their immune system. Mammalian hosts react to infections with an innate response, often involving inflammation, followed by an adaptive response.

An allergic reaction, formally known as type 1 hypersensitivity, is the result of an inappropriate immune response triggering inflammation. A common example is hay fever, which is caused by a hypersensitive response by skin mast cells to allergens. Pre-sensitized mast cells respond by degranulating, releasing vasoactive chemicals such as histamine. These chemicals propagate an excessive inflammatory response characterized by blood vessel dilation, production of pro-inflammatory molecules, cytokine release, and recruitment of leukocytes. Severe inflammatory response may mature into a systemic response known as anaphylaxis. Another common example is food allergies, such as nut allergies (e.g., peanut).

Other hypersensitivity reactions (type 2 and type 3) are mediated by antibody reactions and induce inflammation by attracting leukocytes that damage surrounding tissue.

Inflammatory myopathies are caused by the immune system inappropriately attacking components of muscle, leading to signs of muscle inflammation. They may occur in conjunction with other immune disorders, such as systemic sclerosis, and include dermatomyositis, polymyositis, and inclusion body myositis.

Autoimmune Disease and/or Inflammation Arising Therefrom

Autoimmune diseases arise from an abnormal immune response of the body against substances and tissues normally present in the body (autoimmunity). This may be restricted to certain organs (e.g. in autoimmune thyroiditis) or involve a particular tissue in different places (e.g. Goodpasture's disease which may affect the basement membrane in both the lung and the kidney). The treatment of autoimmune diseases is typically with immunosuppression-medication that decreases the immune response.

A number of autoimmune diseases are recognized, including but not limited to: Acute disseminated encephalomyelitis (ADEM); Addison's disease; Agammaglobulinemia; Alopecia areata; Amyotrophic lateral sclerosis (Lou Gehrig's disease; Motor Neuron Disease); Ankylosing Spondylitis; Antiphospholipid syndrome; Antisynthetase syndrome; Atopic allergy I; Atopic dermatitis I; Autoimmune aplastic anemia; Autoimmune cardiomyopathy; Autoimmune enteropathy; Autoimmune hemolytic anemia; Autoimmune hepatitis; Autoimmune inner ear disease; Autoimmune lymphoproliferative syndrome; Autoimmune pancreatitis; Autoimmune peripheral neuropathy; Autoimmune polyendocrine syndrome; Autoimmune progesterone dermatitis; Autoimmune thrombocytopenic purpura; Autoimmune urticaria; Autoimmune uveitis; Balo disease/Balo concentric sclerosis; Behcet's disease; Berger's disease; Bickerstaff's encephalitis; Blau syndrome; Bullous pemphigoid; Cancer; Castleman's disease; Celiac disease; Chagas disease; Chronic inflammatory demyelinating polyneuropathy;

Chronic obstructive pulmonary disease; Chronic recurrent multifocal osteomyelitis; Churg-Strauss syndrome Cicatricial pemphigoid; Cogan syndrome; Cold agglutinin disease; Complement component 2 deficiency; Contact dermatitis; Cranial arteritis; CREST; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Fibrodysplasia ossificans progressive; Fibrosing alveolitis (or Idiopathic pulmonary fibrosis); Gastrointestinal pemphigoid; Glomerulonephritis; Goodpasture's syndrome; granulomatosis with polyangiitis; Graves' disease; Guillain-Barré syndrome (GBS); Hashimoto's encephalopathy; Hashimoto's thyroiditis; Henoch-Schonlein purpura; Herpes gestationis; Hidradenitis suppurativa; Hughes-Stovin syndrome; Hypogammaglobulinemia; Idiopathic inflammatory demyelinating diseases (a variant of multiple sclerosis); Idiopathic pulmonary fibrosis; Idiopathic thrombocytopenic purpura; Inclusion body myositis; Chronic inflammatory demyelinating polyneuropathy; Interstitial cystitis; Juvenile idiopathic arthritis; Kawasaki's disease; Lambert-Eaton myasthenic syndrome; Leukocytoclastic vasculitis; Lichen planus; Lichen sclerosus; Linear IgA disease (LAD); Lupoid hepatitis; Lupus erythematosus; Majeed syndrome; Ménière's disease; Miller-Fisher syndrome; Mixed connective tissue disease; Morphea; Mucha-Habermann disease; Multiple sclerosis; Myasthenia gravis; Microscopic colitis; Myositis; Narcolepsy; Neuromyelitis optica; Neuromyotonia; Ocular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Parsonage-Turner syndrome; Pars planitis; Pemphigus vulgaris; Pernicious anaemia; Perivenous encephalomyelitis; POEMS syndrome; Polyarteritis nodosa; Polymyalgia rheumatic; Polymyositis; Primary biliary cirrhosis; Primary sclerosing cholangitis; Progressive inflammatory neuropathy; Psoriasis; Psoriatic arthritis; Pyoderma gangrenosum; Pure red cell aplasia; Rasmussen's encephalitis; Raynaud phenomenon; Relapsing polychondritis; Reiter's syndrome; Rheumatic fever; Sarcoidosis; Schizophrenia; Schmidt syndrome; Schnitzler syndrome; Scleritis; Scleroderma; Serum Sickness; Sjögren's syndrome; Spondyloarthropathy; Still's disease; Stiff person syndrome; Subacute bacterial endocarditis; Susac's syndrome; Sweet's syndrome; Sydenham chorea; Sympathetic ophthalmia; Systemic lupus erythematosus; Takayasu's arteritis; Temporal arteritis; Thrombocytopenia; Tolosa-Hunt syndrome; Transverse myelitis; Ulcerative colitis; Undifferentiated connective tissue disease; Undifferentiated spondyloarthropathy; Urticarial vasculitis; Vasculitis; and Vitiligo.

Multiple sclerosis (MS), also known as disseminated sclerosis or encephalomyelitis disseminata, is an inflammatory disease in which the insulating covers of nerve cells in the brain and spinal cord are damaged. This damage disrupts the ability of parts of the nervous system to communicate, resulting in a wide range of signs and symptoms, including physical, mental, and sometimes psychiatric problems. MS takes several forms, with new symptoms either occurring in isolated attacks (relapsing forms) or building up over time (progressive forms). Between attacks, symptoms may disappear completely; however, permanent neurological problems often occur, especially as the disease advances.

While the cause is not clear, the underlying mechanism is thought to be either destruction by the immune system or failure of the myelin-producing cells. Proposed causes for this include genetics and environmental factors such as infections. MS is usually diagnosed based on the presenting signs and symptoms and the results of supporting medical tests.

Treatments attempt to improve function after an attack and prevent new attacks. Medications used to treat MS while modestly effective can have adverse effects and can be poorly tolerated. Many people pursue alternative treatments, despite a lack of evidence. The long-term outcome is difficult to predict, with good outcomes more often seen in women, those who develop the disease early in life, those with a relapsing course, and those who initially experienced few attacks. Life expectancy is on average 5 to 10 years lower than that of an unaffected population.

Multiple sclerosis is the most common autoimmune disorder affecting the central nervous system. As of 2008, between 2 and 2.5 million people are affected globally with rates varying widely in different regions of the world and among different populations. The disease usually begins between the ages of 20 and 50 and is twice as common in women as in men.

Apart from demyelination, the other sign of the disease is inflammation. Fitting with an immunological explanation, the inflammatory process is caused by T cells. T cells gain entry into the brain via disruptions in the blood-brain barrier. The T cells recognize myelin as foreign and attack it, explaining why these cells are also called "autoreactive lymphocytes."

The attack of myelin starts inflammatory processes, which triggers other immune cells and the release of soluble factors like cytokines and antibodies. Further breakdown of the blood-brain barrier, in turn cause a number of other damaging effects such as swelling, activation of macrophages, and more activation of cytokines and other destructive proteins. Inflammation can potentially reduce transmission of information between neurons in at least three ways. The soluble factors released might stop neurotransmission by intact neurons. These factors could lead to or enhance the loss of myelin, or they may cause the axon to break down completely.

Treating or Preventing Inflammation or Autoimmune Disease

Disclosed herein are methods of treating or preventing inflammation or an autoimmune disease or symptom thereof in a subject need thereof comprising administering an effective amount of EPS to said subject.

The appropriate dosage of EPS will depend, for example, on the condition to be treated, the severity and course of the condition, whether the EPS is administered for preventive or therapeutic purposes, previous therapy, the patient's clinical history and response to EPS, the type of EPS used, and the discretion of the attending physician. EPS is suitably administered to the patient at one time or over a series of treatments and may be administered to the patient at any time as necessary for treatment or prevention of disease/disorder. EPS may be administered as the sole treatment or in conjunction with other drugs or therapies useful in treating the condition in question.

Routes of Administration

EPS can be administered systemically or locally. The route of administration used can depend upon the disease/disorder being treated or prevented.

In various embodiments, the route of administration can be auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, dental, intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, larynaeal, nasal, nasogastric, not applicable, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanicureteral, urethral, vaginal, or by other method or any combination of the forgoing as would be known to one of ordinary skill in the art (see, for example, Remington's Pharmaceutical Sciences, 18th Ed. Mack Printing Company, 1990, incorporated herein by reference).

Formulations and Dosage Forms

EPS can be provided in a pharmaceutical composition. The pharmaceutical composition can comprise pharmaceutically acceptable diluent(s), excipient(s), or carrier(s). The pharmaceutical compositions cm include other medicinal or pharmaceutical agents, carriers, adjuvants, such as preserving, stabilizing, wetting or emulsifying agents, solution promoters, salts for regulating the osmotic pressure, and/or buffers.

Methods well known in the art for making formulations are to be found in, for example, Remington: The Science and Practice of Pharmacy, (20th ed.) ed. A. R. Gennaro A R., 2000, Lippencott Williams & Wilkins. Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

The concentration of EPS in the formulations can vary depending upon a number of issues, including the dosage to be administered, and the route of administration.

EXAMPLES

Example 1: Protection from Intestinal Inflammation by Bacterial Exopolysaccharides Introduction The gastrointestinal microbiota contributes to the development and maintenance of the host immune system. One benefit of a healthy microbiota is protection from colitis induced by enteric pathogens as well as by inflammatory agents such as dextran sulfate or 2,4,6-trinitrobenzene sulfonic acid (1-3). Although much work has been done to identify specific bacteria that prevent colitis, many questions remain about the mechanisms by which these bacteria elicit a protective response. It was previously shown that a single oral dose of *Bacillus subtilis* protects mice from disease induced by the enteric pathogen *Citrobacter rodentium* (4), which shares many characteristics with the human pathogen enteropathogenic *Escherichia coli*. Symptoms of infection include diarrhea, systemic increases in proinflammatory cytokines, and altered colonic architecture, such as crypt hyperplasia, goblet cell depletion, and infiltration of immune cells, including neutrophils and T cells. However, mice administered *B. subtilis* in addition to *C. rodentium* display no evidence of diarrhea, have normal levels of proinflammatory cytokines, and normal colonic architecture (4).

During infection, *C. rodentium* disrupts the intestinal barrier (5), resulting in translocation of lumenal contents and activation of the host pattern recognition receptors, which include TLRs. TLRs recognize conserved motifs of microbial proteins (e.g., flagella), lipids (e.g., LPS), and nucleic acids (e.g., CpG) as well as host danger-associated molecular patterns (6). Activation of TLRs results in translocation of NF-kB to the nucleus, production of chemokines and cytokines, and ultimately recruitment of immune cells to the site of infection (6). This inflammatory cascade is needed to clear the pathogen, but it also damages the host tissues (7-9). For example, MyD88 knockout (KO) mice do not develop colonic hyperplasia or recruit neutrophils but succumb to infection. In contrast, most immunocompetent strains of mice clear *C. rodentium* 3-4 wk postinfection.

*B. subtilis* is a Gram-positive spore-forming bacterium present in the gastrointestinal tract of both humans and mice (10, 11). Several groups report that select probiotic strains of *B. subtilis* relieve the symptoms associated with antibiotic-associated diarrhea and irritable bowel syndrome in human patients; however the mechanisms of protection have not been well established (10, 11). In a previous study, it was determined that an exopolysaccharide (EPS) mutant failed to prevent *C. rodentium*-associated disease, suggesting that EPS are the bacterial components mediating protection (4). EPS are secreted heterogeneous structures composed primarily of carbohydrates that not only sometimes coat bacteria but are major components of the biofilm matrix (12). The role of EPS during pathogen infection is well appreciated. For example, pathogenic *Staphylococcus aureus* are coated with an EPS-containing capsule that prevents phagocytosis and allows adherence of the bacteria to host tissues and subsequent immune evasion (13). Less understood is the role of bacterial EPS during probiosis. EPS may play a role in probiotic or commensal organisms to establish and maintain an intestinal niche that could prevent pathogen colonization. Alternatively, gut metabolism of EPS could contribute to short chain fatty acid synthesis, a process that regulates intestinal permeability (14). Interestingly, a few groups have demonstrated that EPS suppress disease by modulating the host inflammatory response via TLR2 signaling (1, 2). Collectively, these studies suggest that bacterial EPS, such as those produced by *B. subtilis*, could prevent intestinal disease using one or more of several different mechanisms, including alteration of pathogen colonization, reduction of gut permeability, and immunomodulation of the host response. Herein it is demonstrated that *B. subtilis* treatment did not alter pathogen colonization nor prevent disruption of the epithelium, but instead, protection by *B. subtilis* EPS is a result of host immune modulation. After purifying EPS and showing that they mediate protection, host immune cells were identified that bind EPS and further showed that protection includes TLR4 and MyD88-signaling myeloid cells. Furthermore, cells from wild-type (wt) and TLR4 KO mice were adoptively transferred to naive wt mice to test whether these cells conveyed protection from enteric disease caused by *C. rodentium* and to identify which cells use TLR4. These studies identify bacterial polysaccharides, which after a single injection, have the capacity to prevent colitis in an infectious disease model in a TLR4-dependent manner.

Materials and Methods

Reagents and Mice

Anti-F4/80 (clone BM8) and anti-CD11b (clone M1/70) were obtained from BioLegend (San Diego, Calif.); donkey anti-rabbit Ig was obtained from The Jackson Laboratory (Bar Harbor, Me.). All other reagents were purchased from Sigma-Aldrich unless otherwise noted. All animal experiments were performed according to protocols approved by the Institutional Animal Care and Usage Committee at Loyola University Medical Center (Maywood, Ill.). Specific pathogen-free C57BL/6, MyD88 KO, and TLR4 KO founders were purchased from The Jackson Laboratory. Mice lacking MyD88 in myeloid cells and epithelial cells were generated by crossing a Lyz2-Cre or Villin-Cre transgenic mouse, respectively, to a MyD88 foxed mouse as described previously (15). Mice used for these experiments (4-8 wk of age) were bred at Loyola University Chicago. Sterile standard chow and tap water were given to mice ad libitum.

Bacterial and Spore Preparation wt *B. subtilis* 3610 spores were germinated via exhaustion as described previously (4). On the day of administration, *B. subtilis* spores were washed with ice-cold water, resuspended in 100 ml PBS, and administered to mice via oral gavage. For infection studies, *C. rodentium* ATCC 51459 was cultured for 16 h in Luria-Bertani medium and washed once in PBS, and an infectious dose was resuspended in 100 ml sterile PBS for administration to mice by oral gavage. MyD88 KO and epithelial MyD88-deficient mice received $10^7$ CFUs; all other mouse strains received $5\times10^8$ CFUs pathogen.

In Vivo Imaging of *C. rodentium*

As previously described (5), *C. rodentium* ICC180 (*C. rodentium* lux+) was grown overnight at 37° C. in Luria-Bertani medium and orally gavaged into C57BL/6 mice (~$5\times10^8$ CFU/mouse). Assessment of bioluminescence (photons $s^{-1}$ $cm^{-2}$ $sr^{-1}$) in living animals was measured using the IVIS100 system (Xenogen, Alameda, Calif.). A photograph (grayscale reference image) was taken under low illumination prior to quantification of photons emitted from *C. rodentium* ICC180 (medium binning, 5-min exposure) using the software program Living Image (Xenogen). A pseudocolor heat map image representing light intensity (blue [least intense] to red [most intense]) was generated using Living Image software and superimposed over the grayscale reference image.

*C. rodentium* Colonization

*C. rodentium* colonization was assessed in fresh fecal samples homogenized in 500 ml sterile 20% glycerol in PBS. For mucosal studies, colonic fecal contents were removed and the tissue flushed with sterile PBS. The colon was homogenized in 2 ml sterile 20% glycerol in PBS. Serial dilutions were cultured on selective MacConkey plates for 16 h at 37° C.; only colonies that displayed the characteristic pink center surrounded by a white rim (*C. rodentium*) were counted. Colonization was calculated and expressed as CFUs per gram feces.

Exopolysaccharide Preparation

Exopolysaccharides were isolated from *B. subtilis* DS991 (sinRtasA mutant), a strain that produces and secretes large amounts of EPS; material from this strain is designated EPS+ (16). As a control, DS5187 (sinRtasAepsH mutant) was used, a strain that does not produce EPS (16) and material from this strain is referred to as EPS−. EPS were isolated as described previously (16). Briefly, stationary phase supernatants were mixed with an equal volume of 100% EtOH at 4° C. for 90 min to precipitate the EPS. The precipitant was pelleted (15,000×3 g, 4° C., 20 min), washed in PBS, and resuspended in 0.1 M Tris. Samples were digested with DNase (67 mg/ml) and RNase (330 µg/ml) at 37° C.; after 1 h, proteinase K (40 mg/ml) was added, and samples were incubated at 55° C. for 1 h. EPS was EtOH precipitated, resuspended in 0.1 M Tris (pH 8), and further purified by gel filtration on an S1000 column in 0.1 M Tris (pH 8) and then desalted by dialysis. EPS was quantified by a colorimetric phenol sulfuric acid assay using serial dilutions of fructose as standard (17). Sample purity was assessed by immunoelectrophoresis and Western blot analysis using anti-EPS antiserum.

Composition and Linkage Analysis of EPS

These analyses were performed at the Complex Carbohydrate Research Center (University of Georgia) (18). Gas chromatography/mass spectrometry analysis of per-O-trimethylsilyl derivatives of the monosaccharide methyl glycosides was performed on an Agilent 7890A GC interfaced to a 5975C MSD, using an Agilent DB-1 fused silica capillary column (30 m×0.25 mm ID) and linkages were determined on an Agilent 7890A GC interfaced to a 5975C MSD (mass selective detector, electron impact ionization mode); separation was performed on a Supelco 2380 fused silica capillary column (30 m×0.25 mm ID).

Generation of EPS-Specific Abs

A New Zealand White rabbit was immunized by i.m. and s.c. injection of 100 µg EPS in TiterMax Gold adjuvant. Three weeks post primary immunization, the rabbit was boosted with 100 µg EPS in adjuvant. Eight days later, serum was collected. Ab to EPS was detected by Western blot analysis using donkey anti-rabbit (H&L)-HRP (The Jackson Laboratory) Abs as secondary Ab and by immunoelectrophoresis followed by staining with Coomassie brilliant blue to visualize Ag/Ab arcs of precipitation.

Study Design

*B. subtilis* spores ($10^9$ in 100 µl PBS, orally administered) or 200 µl EPS (1 mM in 0.1 M Tris, i.p.) or hyaluronic acid (PBS, i.p.) were administered to mice 24 h prior to infection with *C. rodentium* by oral gavage. Age- and gender-matched mice were used for each experiment. To assess disease, all mice were euthanized 10 or 11 d postinfection (dpi) and tissues were collected, except for the MyD88 KO mice, which were euthanized 9 dpi. These days were chosen because at these times the pathogen is well established in each strain and colitis is evident (7-9). Before euthanization, blood was collected. Serum keratinocyte-derived cytokine (KC) levels were assessed by ELISA (R&D Systems, Minneapolis, Minn.). To assess diarrhea, feces were examined and scored 1-4 (19): 1, no diarrhea (hard, dry pellets); 2, slightly soft stool (mild diarrhea); 3, very soft stool (moderate diarrhea); and 4, unformed stool (severe diarrhea). Distal colons were collected and processed for histological analysis as follows: colons were fixed overnight in 10% formalin buffered phosphate, dehydrated through an alcohol gradient, cleared with xylene, and infiltrated with paraffin. Tissues were sectioned longitudinally at 4 µm and stained with H&E. Epithelial hyperplasia in the distal colon was determined from images of each colon taken with a Leica DM IRB microscope equipped with MagnaFire charge-coupled device camera as described previously (20). Five well-oriented crypt heights/mouse were measured from two to three regions.

Assessment of EPS Binding to Cells

Peritoneal cells were obtained from mice (4-6 wk of age) injected i.p. with 5 ml DMEM (10% FBS). After lysing RBCs, cells were incubated with EPS, washed, and then incubated with anti-F4/80 (clone BM8), anti-CD11b (clone M1/70), or anti-EPS, followed by donkey anti-rabbit Ig as secondary Ab. Fluorescence intensity was assessed by flow cytometry.

Assessment of EPS-Induced Cytokine Production

Peritoneal cells were obtained from euthanized mice (4-6 wk of age) injected i.p. with 5 ml DMEM (10% FBS). After lysing RBCs, cells were incubated with EPS (5, 15, or 30 µg/ml), LPS (100 ng/ml), or $Pam_3Cys_4$ (100 ng/ml), and supernatant was collected at 2 and 6 h for measurement of KC and TNF-a, respectively, by ELISA. As a control, the same volume of material from the non-EPS-producing strain was used.

Transfer Studies

Peritoneal cells were isolated from mice (4-6 wk of age) injected i.p. with 5 ml DMEM (10% FBS) 2 to 3 d posttreatment with EPS (i.p.). Cells ($6\times10^4$) were injected (300 µl, i.p.) into naive mice (4-6 wk of age) at +1, −1, and −3 dpi with C. rodentium.

Statistical Analysis

All experiments were performed a minimum of three times and analyzed using the Student t test. Error bars denote SEM. Differences were considered statistically significant if $p<0.05$.

Results

Figure 1B:
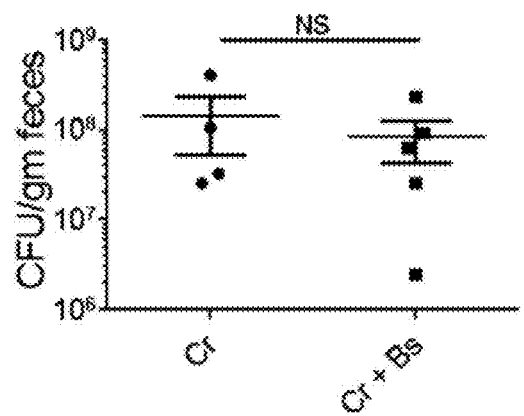
Figure 1C:
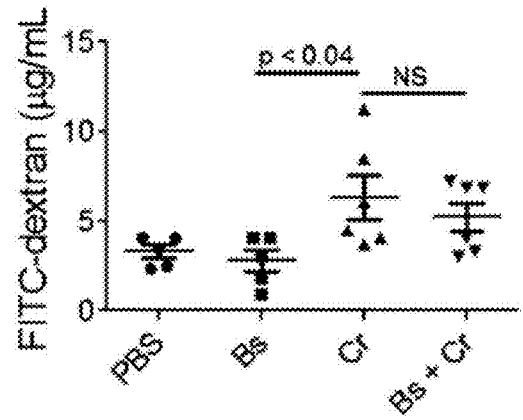
Figure 2A:
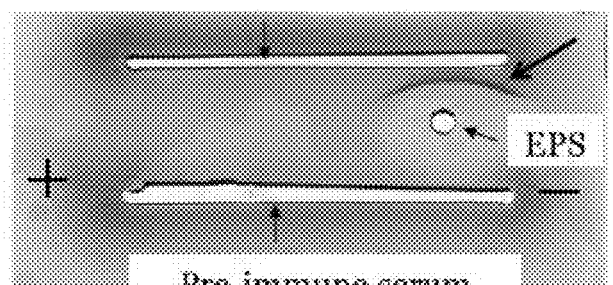
FIGS. 2A-H depict assessment of the B. subtilis exopolysaccharides on C. rodentium-associated disease 10 d postinfection (dpi) of wt mice. (A) Immunoelectrophoresis analysis of purified EPS (arrow points to precipitation arc). (B) Average colonic crypt heights from each treatment group. Serum KC levels (C) and evidence of diarrhea (D) were also used as disease markers. Results are averages from at least three independent experiments; a total of 5-12 mice were assessed for each group. EPS+, exopolysaccharide from B. subtilis strain DS991; EPS−, material from B. subtilis strain DS5187; Cr, C. rodentium. Representative images of H&E-stained colons from wt mice (original magnification ×100). Images are representative of mice that received EPS from DS991 prior to C. rodentium infection (E) or material from the non-EPS producing strain DS5187 prior to pathogen infection (F). Representative images from myeloid MyD88 KO mice (G) and epithelial MyD88 KO mice (H) treated with EPS prior to infection with C. rodentium.
Figure 2B:
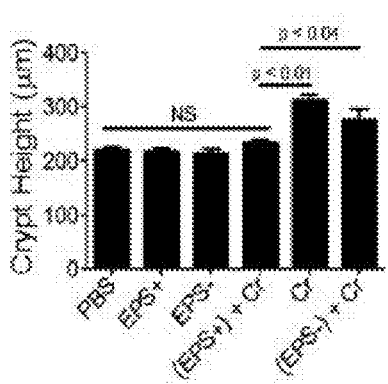
Figure 2C:
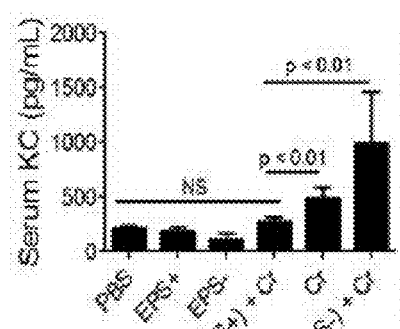
Figure 2D:
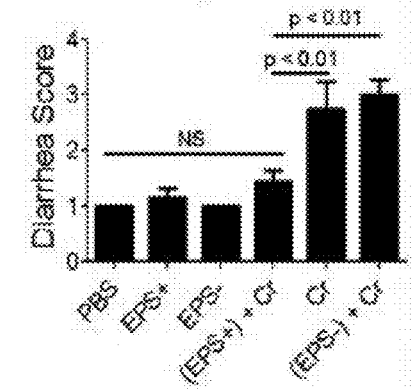
Figure 2E:
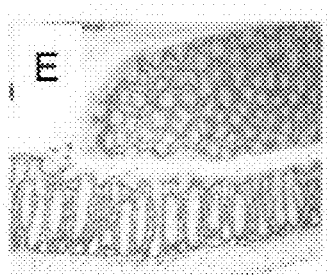
Figure 2F:
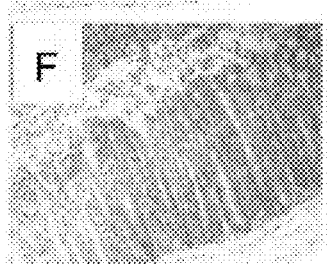
Figure 2G:
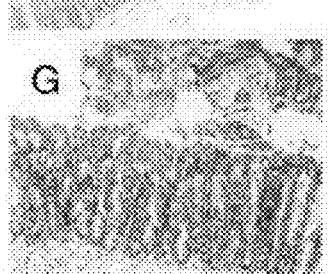
Figure 2H:
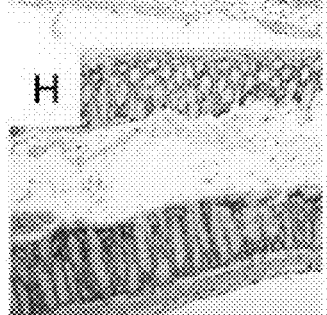
Figure 3A:
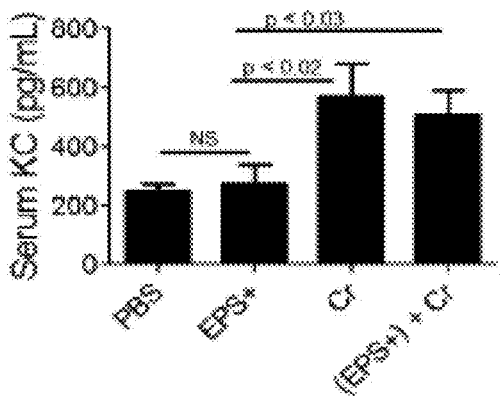
FIGS. 3A-F depict assessment of C. rodentium-associated disease in EPS treated TLR4 KO mice or TLR4 agonist-treated wt mice. Quantification by ELISA of proinflammatory KC in serum of TLR4 KO mice infected with C. rodentium (Cr) with or without EPS (EPS+); PBS and EPS+ are negative controls (A). Summary of colonic crypt heights from each treatment group (B). Diarrhea (C) also served as a disease marker. Results are averages from at least three independent experiments; a total of 5-10 mice were assessed for each group. (D-F) wt mice were treated with 50, 100, or 150 μg of the TLR4 agonist hyaluronic acid (HA) prior to infection and then assessed for disease 10 dpi. Serum KC was measured by ELISA (D), colonic crypt heights from each treatment group were measured (E), and diarrhea (F) also served as a disease marker. Results are averages from at two independent experiments; a total of four to five mice were assessed for each group.
Figure 3D:
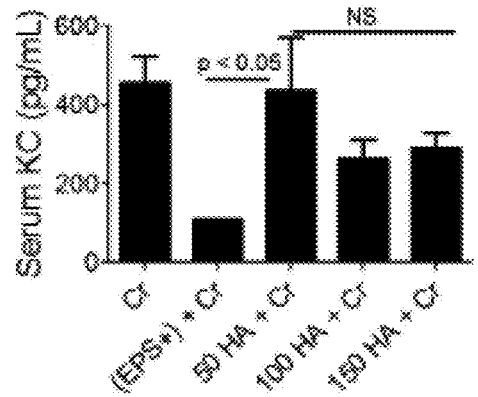
Figure 3B:
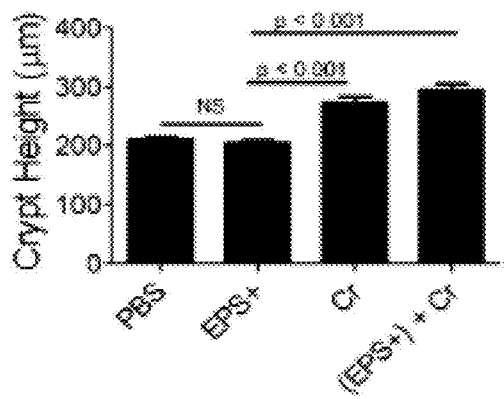
Figure 3E:
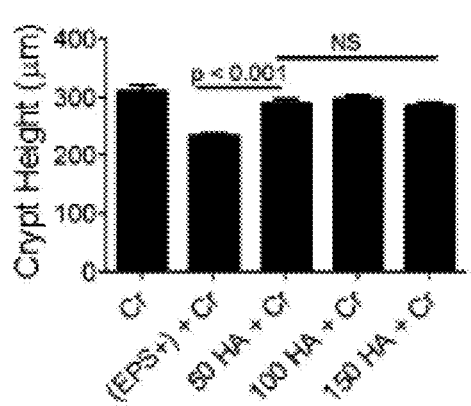
Figure 3C:
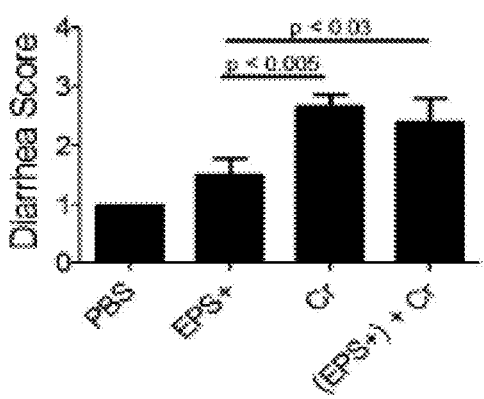
Figure 3F:
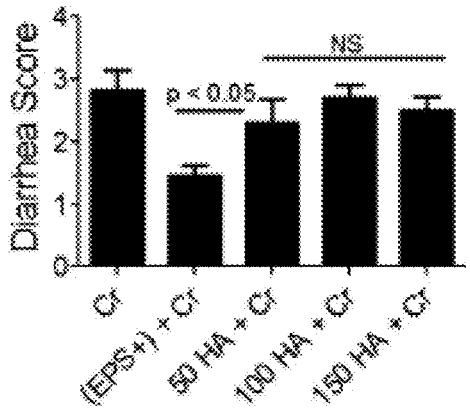
Figure 4A:
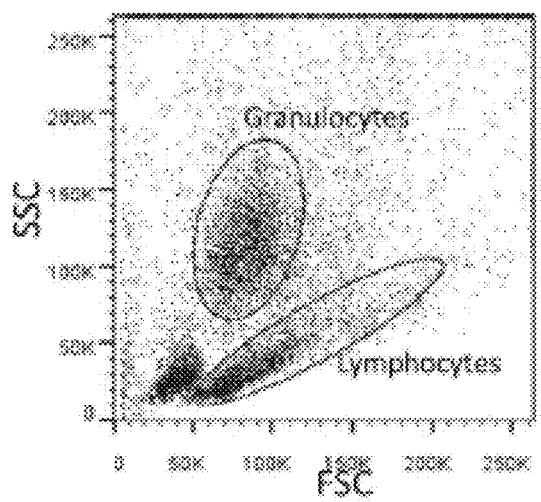
FIGS. 4A-D depict flow cytometric analysis of EPS-binding to peritoneal cells from wt and TLR4 KO mice. FSC versus SSC (A); granulocyte and lymphocyte binding to EPS (B)—gray peak is negative isotype control; staining of wt or TLR4 KO F4/80$^+$CD11b$^+$ gated cells with EPS (C, D). Fluorescence intensity represents EPS binding. Data shown are from one of three independent experiments.
Figure 4B:
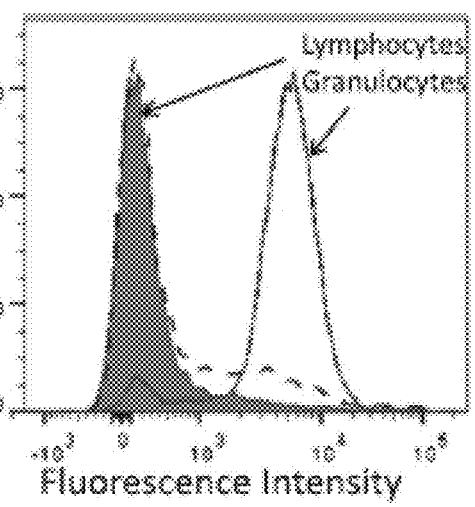
Figure 4C:
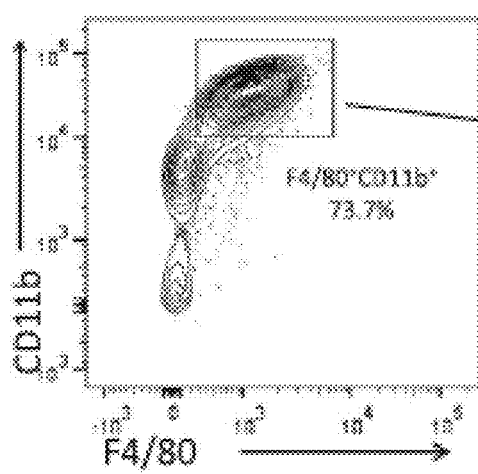
Figure 4D:
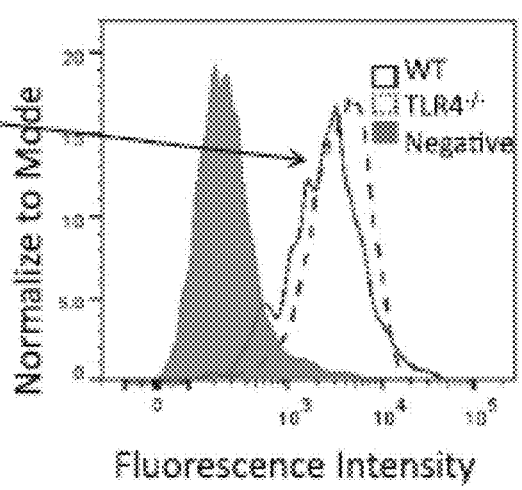

Effect of B. subtilis on C. rodentium Colonization and Pathogen-Induced Gut Leakiness B. subtilis could prevent disease by altering pathogen adherence and/or colonization, by maintaining epithelial barrier integrity, or by changing the host inflammatory response. To test whether pathogen colonization was altered in the presence of B. subtilis, in vivo imaging was performed using $lux^+$ C. rodentium as well as traditional plating techniques. Mice were orally administered B. subtilis ($10^9$ CFU), followed 24 h later by C. rodentium ($5\times10^8$ CFU), and the $lux^+$ C. rodentium was detected during the course of disease using an in vivo imaging system. It was found that administration of B. subtilis did not change the localization or quantity of luminescence of C. rodentium. The quantity of adherent and lumenal C. rodentium was assessed by plating colonic (adherent) and fecal (lumenal) samples and no differences were observed when mice were treated with B. subtilis (FIG. 1, panels A and B). These data suggest that B. subtilis does not protect mice by altering the localization, adherence, or density of the pathogen.

To test whether B. subtilis prevents disease by maintaining epithelial barrier integrity, FITC-dextran was orally administered to mice and then the serum was assessed for fluorescence. If B. subtilis functions by preventing epithelial damage, then little to no FITC-dextran in serum should be detected. However, it was found that mice infected with C. rodentium as well as those that received B. subtilis prior to pathogen infection had increased quantities of serum FITC-dextran (6.3 and 5.2 µg/ml, respectively) when compared with PBS-treated control mice (3.3 ng/ml) (FIG. 1, panel C). These data suggest that B. subtilis does not protect from C. rodentium-induced colitis by preventing pathogen-induced disruption of the epithelium.

Analysis of EPS Composition and Structure

Because an epsH mutant, which does not produce EPS, failed to protect mice from C. rodentium-induced disease (7), it was hypothesized that EPS may have immunomodulatory activity. To begin to test this idea, EPS was isolated and its structure analyzed. EPS were purified from the sinRtasA mutant (DS991), which overproduces and secretes EPS into the supernatant (EPS+); as a control, supernatant of the sinRtasAepsH mutant (DS5187), which is unable to synthesize EPS (8), was subjected to the same purification process (EPS−). The purity of EPS were assessed by immunoelectrophoresis and Western blot analysis using rabbit anti-EPS antiserum. By immunoelectrophoresis, only a single precipitation arc was observed (FIG. 2, panel A); no bands were observed with preimmune serum or with the EPS− material (data not shown). By Western blot analysis, only a single band of the expected size (~300 kDa) was produced by the EPS⁻ strain. The OD280 and OD260 of purified EPS at a concentration of 1 mg/ml was 0.091 and 0.013, respectively, indicating that EPS were contaminated by little to no protein or nucleic acid.

The structure of purified EPS was analyzed by gas chromatography/mass spectrometry at the Complex Carbohydrate Research Center (University of Georgia), and the carbohydrate portion was found to be primarily mannose (88%) and glucose (11.9%) (Table I). Further structural analysis to determine the carbohydrate linkages revealed that the primary linkages are 2,6-mannose (31.8%), terminal mannose (29.9%), 3-mannose (15%), 2-mannose (4.7%), 6-mannose (4.7%), 6-glucose (3.7%), and terminal glucose (3.5%) (Table II); these data are consistent with the compositional analysis that indicates that mannose is the primary component of EPS.

TABLE I

Analysis of EPS composition

| Glycosyl Residue | Mass (µg) | Molecular Percentage[a] |
|---|---|---|
| Ribose | ND | — |
| Arabinose | ND | — |
| Rhamnose | ND | — |
| Fucose | ND | — |
| Xylose | ND | — |
| Glucuronic acid | ND | — |
| Galacturonic acid | ND | — |
| Mannose | 250.6 | 88.0 |
| Galactose | ND | — |
| Glucose | 33.9 | 11.9 |
| N-Acetylgalactosamine | ND | — |
| N-Acetylglucosamine | 0.2 | 0.1 |
| N-Acetylmannosamine | ND | — |
| Σ = | 284.7 | 100 |

[a]Values are expressed as mole percent of total carbohydrate. The total percentage may not add up to exactly 100% because of rounding.

TABLE II

Linkage analyses of EPS by gas chromatograph and mass spectroscopy

| Glycosyl Linkage Residue | EPS % Present |
| --- | --- |
| 2-Rhamnopyranosyl residue (2-Rha) | 0.1 |
| Terminal Mannopyransosyl residue (t-Man) | 29.9 |
| Terminal Glucopyranosyl residue (t-Glc) | 3.5 |
| 3 linked Glucopyranosyl residue (3-Glc) | 0.2 |
| 2 linked Mannopyranosyl residue (2-Man) | 4.7 |
| 3 linked Mannopyranosyl residue (3-Man) | 15.0 |
| 2 linked Glucopyranosyl residue (2-Glc) | 0.3 |
| 4 linked Mannopyranosyl residue (4-Man) | 0.4 |
| 6 linked Mannopyranosyl residue (6-Man) | 4.7 |
| 6 linked Glucopyranosyl residue (6-Glc) | 3.7 |
| 4 linked Glucopyranosyl residue (4-Glc) | 1.3 |
| 2,3 linked Mannopyranosyl residue (2,3-Man) | 0.3 |
| 3,4 linked Mannopyranosyl residue (3,4-Man) | 0.1 |
| 2,4 linked Mannopyranosyl residue (2,4-Man) | 0.2 |
| 4,6 linked Mannopyranosyl residue (4,6-Man) | 0.2 |
| 3,6 linked Glucopyranosyl residue (3,6-Glc) | 0.3 |
| 3,6 linked Mannopyranosyl residue (3,6-Man) | 0.4 |
| 2,6 linked Mannopyranosyl residue (2,6-Man) | 31.8 |
| 4,6 linked Glucopyranosyl residue (4,6-Glc) | 0.6 |
| 2,6 linked Glucopyranosyl residue (2,6-Glc) | 0.6 |
| 2,3,6 linked Mannopyranosyl residue (2,3,6-Man) | 0.5 |
| 2,4,6 linked Mannopyranosyl residue (2,4,6-Man) | 0.6 |
| 2,3,4,6 linked Mannopyranosyl residue (2,3,4,6-Man) | 0.5 |
| 4 linked N-acetyl Glucosamine (4-GlcNAc) | 0.1 |

Effect of B. subtilis EPS on C. rodentium-Associated Disease

To test whether EPS are sufficient to prevent disease, purified EPS was administered i.p. to wt mice and 24 h later infected them with C. rodentium. Disease was assessed 10 dpi by examining the colon, serum, and feces. Mice that received EPS displayed no evidence of disease (FIG. 2, panels B-E), whereas mice that received material from the non-EPS-producing strain (EPS−), or no treatment other than C. rodentium, had altered colonic architecture (FIG. 2, panels B and F), increased levels of proinflammatory KC (FIG. 2, panel C), and diarrhea (FIG. 2, panel D). These data indicate that EPS from B. subtilis are sufficient to protect wt mice from inflammation postinfection with C. rodentium.

Role of MyD88 and TLR4 in B. subtilis Mediated Protection

Bacterial carbohydrates are ligands for many host pattern recognition receptors, including C-type lectins and TLRs, which are MyD88 dependent. C. rodentium-induced crypt hyperplasia is dependent on MyD88 signaling (9), and because it was observed that B. subtilis and EPS suppressed crypt hyperplasia, it was hypothesized that B. subtilis could mediate protection via this signaling pathway. Because MyD88 KO mice are highly susceptible to C. rodentium and succumb to disease 3-6 dpi (9, 21), the C. rodentium inoculum was titrated and found a minimal dose ($10^7$ CFU) for which all mice developed disease (soft stool) at 5-7 dpi, similar to that observed with wt mice. Postinfection of MyD88 KO mice with C. rodentium ($10^7$ CFU), mice lost weight (8-9 dpi), failed to clear the pathogen, and succumbed to disease by 11 dpi; administration of B. subtilis did not protect mice (data not shown). It is concluded that MyD88 signaling plays a role in B. subtilis-mediated protection of C. rodentium-induced colitis.

To identify the relevant MyD88-dependent TLR needed for protection, individual TLR KO mice were tested for susceptibility to C. rodentium after EPS treatment and started with TLR4 KO. EPS-treated TLR4 KO mice infected with C. rodentium showed evidence of disease including crypt hyperplasia, elevated serum KC, and diarrhea comparable to infected animals without EPS (FIG. 3, panels A-C). As expected, neither material from the (EPS−) strain nor B. subtilis spores protected TLR4 KO mice from disease induced by the enteric pathogen (data not shown). These data suggest that EPS mediate protection via TLR4.

Because TLR4 is required for EPS-mediated protection, it was tested whether a TLR4 agonist, hyaluronic acid was sufficient to prevent C. rodentium-associated disease. Mice were injected with hyaluronic acid (i.p.) prior to infection with C. rodentium, and disease was assessed 10 dpi. Hyaluronic acid did not protect mice at any of the concentrations tested (FIG. 3, panels D-F), indicating that a TLR4 agonist is not capable of, or sufficient for, preventing disease. These data suggest that EPS does not act as a TLR4 agonist but instead may prevent disease by antagonizing TLR4.

Identification of EPS-Binding Cells

Because i.p. administration of EPS prevents C. rodentium-induced colitis, peritoneal cells that bind EPS were searched for by flow cytometry. It was determined that EPS bind cells in the granulocyte gate, with little to no binding to cells in the lymphocyte gate (FIG. 4, panels A and B). More than 70% of cells in the granulocyte gate are $F4/80^+$ $CD11b^+$ macrophages, and it was found that EPS bind nearly all of these peritoneal macrophages (FIG. 4, panels C and D). Although macrophages are "sticky" and readily bind polysaccharides, it is believed that EPS binding is specific because EPS did not bind splenic macrophages, murine macrophage-like RAW264.7 cells or human monocytoid THP-1 cells (data not shown). EPS bound peritoneal macrophages from TLR4 KO mice (FIG. 4, panel D), indicating that although EPS-mediated protection requires TLR4 signaling, EPS either do not bind directly to TLR4 on the peritoneal macrophages or EPS bind to both TLR4 and another receptor.

Effect of EPS on Cytokine Production by wt and TLR4 KO Peritoneal Cells

Figure 5A:
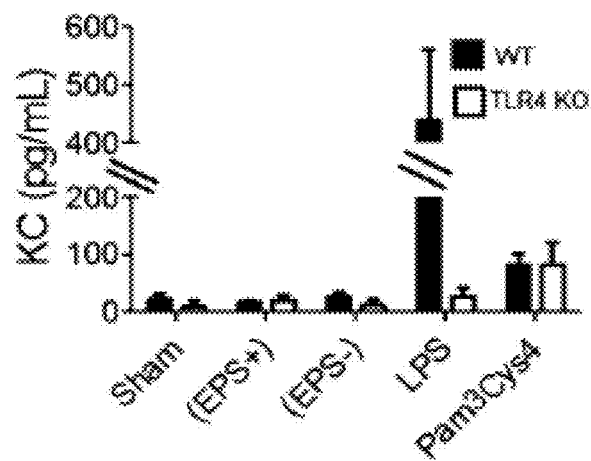
FIGS. 5A-B depict ELISA analysis of cytokines KC (A) and TNF-α (B) induced by in vitro culture of EPS with peritoneal cells from wt and TLR4 KO mice. Peritoneal cells were incubated with EPS (EPS+) (30 μg/ml), material from the non-EPS-producing strain (EPS−), LPS (100 ng/ml), Pam$_3$Cys$_4$ (100 ng/ml), or without addition (sham). Results are average from three independent experiments. ND, not detectable.
Figure 5B:
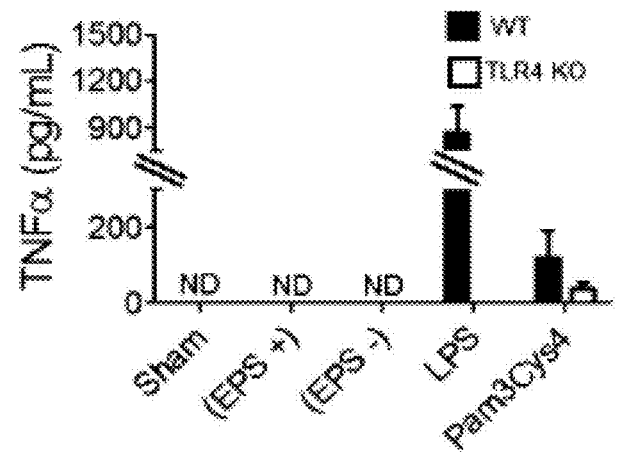
Figure 6A:
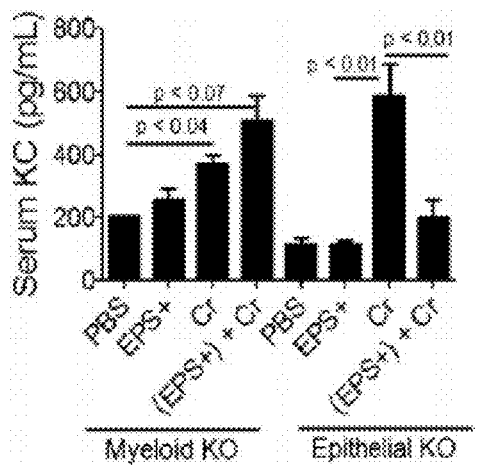
FIGS. 6A-C depict assessment of C. rodentium-associated disease in EPS treated mice lacking MyD88 in myeloid or epithelial cells. Myeloid MyD88 KO and epithelial MyD88 KO mice were treated with EPS (EPS+) (i.p.) 1 d prior to infection with *C. rodentium* (Cr) and disease was assessed 10 dpi. Injection with PBS and EPS+ alone served as negative controls. Serum KC levels (A), colonic crypt height (B), and diarrhea (C) were used as disease markers. Results are averages from at least two independent experiments, and a total of two to five mice were assessed for each group.
Figure 6B:
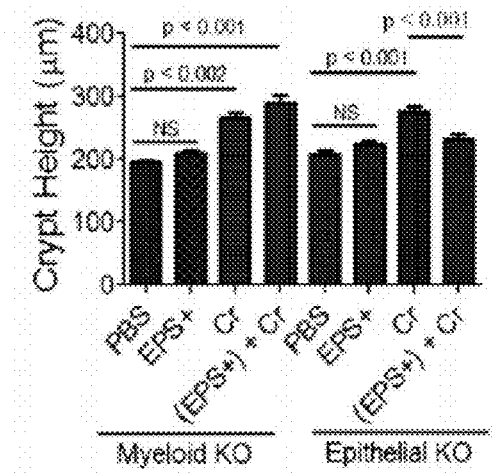
Figure 6C:
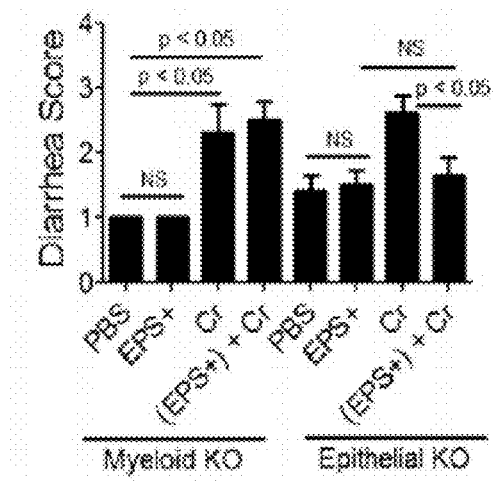
Figure 7A:
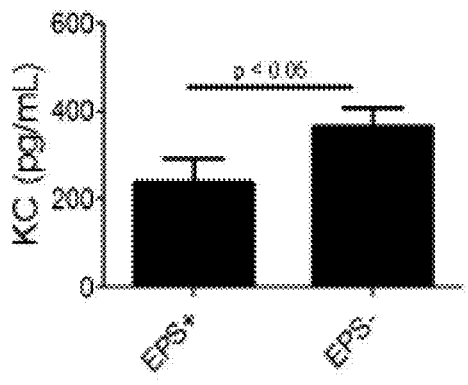
FIGS. 7A-F depict assessment of disease after transfer of peritoneal cells from EPS-treated wt and TLR4 KO mice to *C. rodentium*-infected wt or TLR4 KO mice. Donor wt mice were treated with EPS+ or EPS− material (i.p.) 2-3 d before peritoneal cells ($6 \times 10^4$) were transferred i.p. to naive recipient wt (A-C) mice 1 d prior to, 1 and 3 dpi with *C. rodentium*. Peritoneal cells from wt or TLR4 KO mice similarly treated with EPS+ were transferred i.p. into naive wt or TLR4 KO mice (D-F). Disease was assessed for all mice 10 dpi; serum KC (A, D), crypt hyperplasia (B, E), and diarrhea (C, F) were used as disease markers. KC quantification, crypt height, and diarrhea scores can be compared with uninfected (PBS-treated) mice shown in FIG. 2 on panels B-D. Results are averages from at least three independent experiments and a total of 6-10 mice were assessed for each group.
Figure 7D:
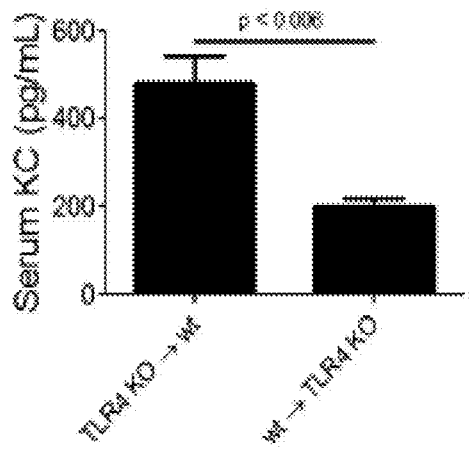
Figure 7B:
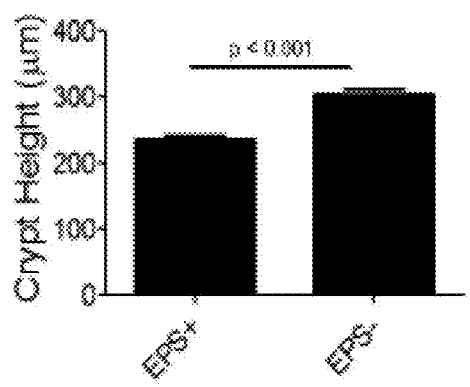
Figure 7E:
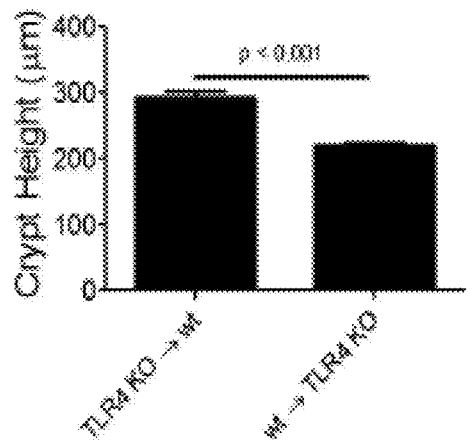
Figure 7C:
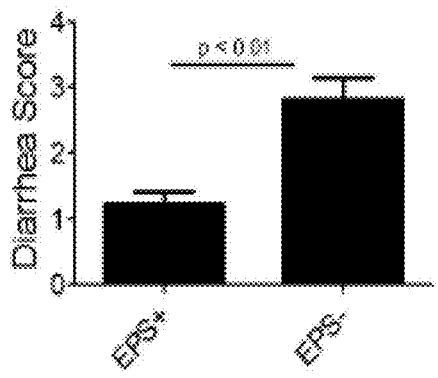
Figure 7F:
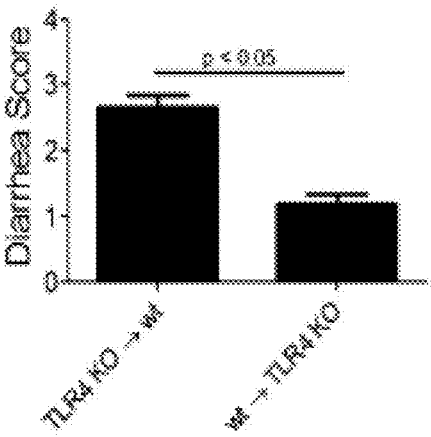

The effect of EPS was examined on peritoneal cells in vitro by incubating EPS with wt or TLR4 KO peritoneal cells and examining cytokine production by ELISA. It was observed that even at high concentrations EPS did not induce KC or TNF-α production by wt or TLR4 KO peritoneal cells (FIG. 5). As expected, wt, but not TLR4 KO, peritoneal cells produced KC and TNF-α when incubated with the TLR4 agonist (LPS), and all cells produced proinflammatory cytokines in response to a TLR2 agonist ($Pam_3Cys_4$). ELISA was also used to test for production of IL-10 by peritoneal cells from EPS-treated mice but found no evidence that EPS induced production of IL-10 (data not shown). These data indicate that EPS does not induce proinflammatory response by peritoneal cells. Similarly, there is no evidence that an IL-10-mediated anti-inflammatory response is stimulated.

Effect of Myeloid-Specific MyD88 Deletion on EPS-Mediated Protection

Because EPS bound peritoneal macrophages and because MyD88 was required for protection, it was hypothesized that mice lacking MyD88 in myeloid cells would be susceptible to C. rodentium-induced disease after treatment with EPS. The amount of C. rodentium needed was titrated to induce disease and determined that $5 \times 10^8$ CFUs, the same infectious dose used with wt mice, was sufficient to induce disease and that at lower doses not all mice were colonized successfully with the pathogen. Mice were treated with EPS (i.p.), and as hypothesized, these mice developed disease (FIGS. 2, panel G and 6), including elevated serum KC, crypt hyperplasia, and diarrhea. Whether EPS could protect mice lacking MyD88 signaling in epithelial cells from *C. rodentium* was also tested, and no disease was observed in these mice (FIGS. 2, panel H and 6), demonstrating that the requirement for MyD88 in myeloid cells is specific. It is concluded that MyD88 signaling by myeloid cells is required for EPS-mediated protection.

Effect of Adoptively Transferred EPS-Treated Peritoneal Cells on Development of *C. Rodentium*-Induced Disease Because it was observed that i.p. administration of EPS prevented disease and because EPS bound peritoneal macrophages, it was hypothesized that peritoneal cells from an EPS-treated mouse could convey protection to naive mice infected with *C. rodentium*. Peritoneal cells were collected by lavage 2-3 d after i.p. injection with EPS+ or EPS−, and $6\times10^4$ cells were injected i.p. into recipient mice on −1, 1, and 3 dpi. Disease was assessed 10 dpi, and no evidence of disease was found in mice that received peritoneal cells from EPS+-treated mice (FIG. 7, panels A-C) when compared with PBS control mice (FIG. 2, panels B-D). In contrast, crypt hyperplasia, elevated KC, and diarrhea were evident in mice that received peritoneal cells treated with material from the non-EPS-producing *B. subtilis* strain (EPS−) (FIG. 7, panels A-C). These data indicate that following treatment with EPS, cells within the peritoneal cavity can suppress inflammation and that this protective effect is only observed with cells from EPS+-treated mice. At the time of transfer, peritoneal cells did not have detectable EPS bound, but instead, the cells bound freshly added EPS (similar to that shown in FIG. 4, panels C and D). It is hypothesized that following EPS administration, EPS are internalized or degraded by host cells and that the protection observed after transfer of peritoneal cells is not due to native EPS transferred with the cells but instead to cells that were activated by the EPS injection.

Because TLR4 signaling plays a role in protection by EPS, it was tested whether peritoneal cells require TLR4 signaling. TLR4 KO and wt mice were treated with EPS, and donor peritoneal cells were transferred into wt or TLR4 KO recipients with the expectation that if TLR4 signaling is required by peritoneal cells to mediate protection, then EPS-treated peritoneal cells from mice lacking TLR4 will not protect wt mice from pathogen-associated disease. As predicted, it was found that EPS-treated TLR4 KO peritoneal cells did not protect wt mice from disease as evidenced by elevated serum KC, crypt hyperplasia, and diarrhea (FIG. 7, panels D-F and PBS controls in FIG. 2, panels B-D). In contrast, TLR4 KO recipient mice were protected by injection of EPS-treated peritoneal cells from wt mice. These data confirm the requirement of TLR4 in the model and suggest that peritoneal cells use TLR4 to mediate protection.

Discussion

The peritoneal cavity contains a variety of host immune cells, the most numerous of which are macrophages (~30-50%) and B cells (~40%) (22). To identify the cells that contribute to protection in the model, cells were searched for that bind EPS and it was found that they bind peritoneal F4/80$^+$CD11b$^+$ macrophages, suggesting a role for macrophages in EPS-mediated protection. Transfer of total peritoneal cells from an EPS-treated mouse was sufficient to protect naive mice from *C. rodentium*-induced enteric inflammation. In contrast, cells from a mouse treated with the EPS− material or TLR4 KO peritoneal cells from EPS-treated mice did not protect mice from disease, demonstrating that EPS and TLR4 signaling play a role in protection. Because EPS do not protect mice that lack MyD88 in myeloid cells, the TLR4-dependent immunosuppressive cells in the peritoneal cavity are likely macrophages.

TLR signaling during *C. rodentium* infection is complex; some TLRs contribute to host defense and others promote host damage (7-9, 21, 23). Previous studies using MyD88 KO mice infected with *C. rodentium* demonstrate that TLR signaling is needed for neutrophil recruitment, for limiting *C. rodentium* translocation, and for epithelial cell repair (9, 21). Interestingly, these mice do not develop crypt hyperplasia (9), suggesting that TLR signaling drives this inflammatory process. In addition, during *C. rodentium* infection, TLR4 signaling promotes disease and inflammation rather than host defense, because development of disease is slightly delayed in TLR4 KO mice, yet these mice clear the pathogen and recover similarly to wt mice (8). This previous study suggests that suppression of TLR4 signaling could alleviate disease, and the data suggest EPS may antagonize TLR4 signaling, because a TLR4 agonist was not capable of protecting mice from disease and EPS do not induce peritoneal cells to produce inflammatory cytokines, which one would expect of a TLR agonist. Interestingly, peritoneal macrophages bind EPS but not directly to TLR4 because EPS binds peritoneal macrophages from TLR4 KO mice. EPS could bind to a protein that is part of the TLR4 signaling complex, such as the ligand binding accessory proteins RP105, CD14, CD36, GD1b, or Dectin-1, and suppress TLR4 signaling, as has been shown for RP105 (24, 25). Alternatively, EPS may bind to mannose-binding receptors, which could cooperate with TLR to initiate an immune response, as described for pathogenic staphylococcyl infections (26).

Other studies have demonstrated that EPS from commensals, *Bacteroides fragilis*, and *Bifidobacterium breve* also can prevent colitis. Immunomodulatory EPS produced by *B. breve* modulate host B cell responses and promote this commensals colonization (27); however, the structure of these EPS are currently unknown. Polysaccharide A (PSA) produced by *B. fragilis*, is composed of a repeating tetrasaccharide moiety and is ~110-130 kDa (28); it has free carboxyl, phosphate, and amino groups that contribute to its zwitterionic nature. PSA is processed by dendritic cells and presented to T cells in an MHC class II-dependent manner and induces anti-inflammatory IL-10-producing regulatory T cells (2, 28, 29). In contrast, *B. subtilis* EPS bind macrophages, and are larger than PSA (0.25 kDa), and likely modulate the host immune response differently than *B. fragilis* PSA.

The probiotic *C. butyricum* promotes development of anti-inflammatory IL-10-producing F4/80$^+$CD11b$^+$CD11c$^{int}$ macrophages, which prevent dextran sulfate-induced colitis (1). In this case, the active bacterial molecules have not been identified. Although protection by *B. subtilis* EPS may be mediated by macrophages, the mechanism is likely different from *B. fragilis* or *C. butyricum* because they require TLR2 signaling whereas *B. subtilis* EPS requires TLR4 signaling. Collectively, the results and previous studies highlight the importance of selective modulation of TLR by commensal and probiotic bacteria to maintain intestinal homeostasis of CD4$^+$ regulatory T cells and macrophages.

It is unknown whether EPS causes an anti-inflammatory response, for example, production of IL-10 or other anti-inflammatory cytokines as is the case with *B. fragilis* and *C. butyricum*, or whether it inhibits induction of the inflammatory response initiated by *C. rodentium* infection. Because in preliminary studies no evidence was found of increased anti-inflammatory cytokines after administration of EPS or *B. subtilis*, it was hypothesized that EPS functions by altering macrophages in a TLR4-dependent manner to generate suppressor M2-like macrophages, which upon injection into wt recipient mice, prevent the inflammatory response caused by *C. rodentium*. Future experiments are needed to elucidate the mechanisms by which EPS and peritoneal macrophages prevent *C. rodentium*-induced colitis.

How can i.p. injection of macrophages suppress inflammation at a distant mucosal site? It is hypothesized that peritoneal macrophages convey protection by one or both of two mechanisms. First, they could secrete a soluble immunosuppressive factor that modulates other immune cells. Alternatively, select peritoneal macrophages may migrate to the colon and suppress pathogen induced colonic inflammation similar to that observed by Fraga-Silva et al. (30) who demonstrated that peritoneal macrophages migrate to areas of fungal infections.

Oral administration of *B. subtilis* provides protection, but administration of EPS by oral gavage does not protect against *C. rodentium*-induced colitis (data not shown). It has previously been shown that protection by *B. subtilis* requires it to be motile (4), and it may be that motile *B. subtilis* localizes to a particular niche in the gut and secretes a concentrated quantity of EPS, whereas administered by oral gavage, EPS do not reach this niche. Alternatively, EPS delivered by oral gavage may be degraded in the ministered up to 3 dpi, a time at which disease has already begun (data not shown), which suggests that EPS may suppress systemic inflammation and be a successful therapeutic in other inflammation models.

Polysaccharides are not the only bacterial molecules with potent immunomodulatory activity. Commensal DNA, sphingolipids from *B. fragilis*, as well as proteins and phospholipids from lactobacilli modulate the host immune system to suppress inflammation (31-33). These studies and that presented herein indicate that commensals produce a variety of factors to maintain immune homeostasis with their host, but studies to identify these important compounds and elucidate their mechanisms of action are in their infancy.

In summary, EPS was identified as the protective agents of *B. subtilis* and it was determined that purified EPS, but not similarly treated material from an EPS– strain, prevent inflammatory disease induced by the enteric pathogen, *C. rodentium*. EPS-mediated protection requires TLR4 signaling, and although TLR signaling is known to regulate pathogen colonization and intestinal permeability, the protective effects of EPS seem to be a result of immunomodulation. Adoptive transfer studies demonstrate that TLR4 signaling on macrophage-rich peritoneal cells is required for EPS-mediated protection. Consistent with the idea that macrophages mediate protection in this model, it was shown that EPS bind peritoneal macrophages and that mice with MyD88-deficient myeloid cells are not protected by EPS. This work highlights how a single dose of purified bacterial molecules, such as EPS, can impact the host immune responses during infection with an enteric pathogen.

BIBLIOGRAPHY

1. Hayashi, A., T. Sato, Kamada, Y. Mikami, Matsuoka, T. Hisamatsu, T. Hibi, A. Roers, H. Yagita, T. Ohteki, et al. 2013. A single strain of *Clostridium butyricum* induces intestinal IL-10-producing macrophages to suppress acute experimental colitis in mice. Cell Host Microbe 13: 711-722.
2. Round, J. L., S. M. Lee, J. Li, G. Tran, B. Jabri, T. A. Chatila, and S. K. Mazmanian. 2011. The Toll-like receptor 2 pathway establishes colonization by a commensal of the human microbiota. Science 332: 974-977.
3. D'Arienzo, R. F. Maurano, Mazzarella, D. Luongo, R. Stefanile, E. Ricca, and M. Rossi. 2006. *Bacillus subtilis* spores reduce susceptibility to *Citrobacter rodentium*-mediated enteropathy in a mouse model. Res. Microbiol. 157: 891-897.
4. Jones, S. E., and K. L. Knight. 2012. *Bacillus subtilis*-mediated protection from *Citrobacter rodentium*-associated enteric disease requires espH and functional flagella. Infect. Immun. 80: 710-719.
5. Wiles, S., K. M. Pickard, K. Peng, T. T. MacDonald, and G. Frankel. 2006. In vivo bioluminescence imaging of the murine pathogen *Citrobacter rodentium*. Infect. Immun. 74: 5391-5396.
6. Taniguchi, Y., N. Yoshioka, K. Nakata, T. Nishizawa, H. Inagawa, C. Kohchi, and G. Soma. 2009. Mechanism for maintaining homeostasis in the immune system of the intestine. Anticancer Res. 29: 4855-4860.
7. Gibson, D. L., C. Ma, C. M. Rosenberger, K. S. Bergstrom, Y. Valdez, J. T. Huang, M. A. Khan, and B. A. Vallance. 2008. Toll-like receptor 2 plays a critical role in maintaining mucosal integrity during *Citrobacter rodentium*-induced colitis. Cell. Microbiol. 10: 388-403.
8. Khan, M. A., C. Ma, L. A. Knodler, Y. Valdez, C. M. Rosenberger, W. Deng, B. B. Finlay, and B. A. Vallance. 2006. Toll-like receptor 4 contributes to colitis development but not to host defense during *Citrobacter rodentium* infection in mice. Infect. Immun. 74: 2522-2536.
9. Gibson, D. L., C. Ma, K. S. Bergstrom, J. T. Huang, C. Man, and B. A. Valiance. 2008. MyD88 signalling plays a critical role in host defence by controlling pathogen burden and promoting epithelial cell homeostasis during *Citrobacter rodentium*-induced colitis. Cell. Microbiol. 10: 618-631.
10. Due Ie, H., H. A. Hong, T. M. Barbosa, A. O. Henriques, and S. M. Cutting. 2004. Characterization of *Bacillus* probiotics available for human use. Appl. Environ. Microbiol. 70: 2161-2171.
11. Hong, H. A., R. Khaneja, N. M. Tam, A. Cazzato, S. Tan, M. Urdaci, A. Brisson, A. Gasbarrini, I. Barnes, and S. M. Cutting. 2009. *Bacillus subtilis* isolated from the human gastrointestinal tract. Res. Microbiol. 160: 134-143.
12. Kearns, D. B., F. Chu, S. S. Branda, R. Kolter, and R. Losick. 2005. A master regulator for biofilm formation by *Bacillus subtilis*. Mol. Microbiol. 55: 739-749.
13. O'Riordan, K., and J. C. Lee. 2004. *Staphylococcus aureus* capsular polysaccharides. Clin. Microbiol. Rev. 17: 218-234.
14. Van Immerseel, F., R. Ducatelle, M. De Vos, N. Boon, T. Van De Wiele, K. Verbeke, P. Rutgeerts, P., B. Sas, P. Louis, and H. J. Flint. 2009. Butyric acid producing anaerobic bacteria as a novel probiotic treatment approach for inflammatory bowel disease. J. Med. Microbiol. 59: 141-143.
15. Gais, P., D. Reim, G. Jusek, T. Rossmann-Bloeck, H. Weighardt, K. Pfeffer, F. Altmayr, K. P. Janssen, and B. Holzmann. 2012. Cutting edge: divergent cellspecific functions of MyD88 for inflammatory responses and organ injury in septic peritonitis. J. Immunol. 188: 5833-5837.
16. Guttenplan, S. B., K. M. Blair, and D. B. Kearns. 2010. The EpsE flagellar clutch is bifunctional and synergizes with EPS biosynthesis to promote *Bacillus subtilis* biofilm formation. PLoS Genet. 6: e1001243.
17. Masuko, T., A. Minami, N. Iwasaki, T. Majima, S. Nishimura, and Y. C. Lee. 2005. Carbohydrate analysis by a phenol-sulfuric acid method in micmplate format. Anal. Biochem. 339: 69-72.

18. York, W. S., A. G. Darvill, M. McNeil, T. T. Stevenson, and P. Albersheim. 1985. Isolation and characterization of plant cell walls and cell-wall components. Methods Enzymol. 118: 3-40.
19. Pant, N., H. Marcotte, H. Br€ussow, L. Svensson, and L. Hammarstrom. 2007. Effective prophylaxis against rotavirus diarrhea using a combination of *Lactobacillus rhamnosus* GG and antibodies. BMC Microbiol. 7: 86.
20. Wu, X., B. A. Vallance, L. Boyer, K. S. Bergstrom, J. Walker, K. Madsen, J. R. O'Kusky, A. M. Buchan, and K. Jacobson. 2008. *Saccharomyces boulardii* ameliorates *Citrobacter rodentium*-induced colitis through actions on bacterial virulence factors. Am. J. Physiol. Gastrointest. Liver Physiol. 294: G295-G306.
21. Lebeis, S. L., B. Bommarius, C. A. Parkos, M. A. Sherman, and D. Kalman. 2007. TLR signaling mediated by MyD88 is required for a protective innate immune response by neutrophils to *Citrobacter rodentium*. J. Immunol. 179: 566-577.
22. Ghosn, E. E., A. A. Cassado, G. R. Govoni, T. Fukuhara, Y. Yana, D. M. Monack, K. R. Bortoluci, S. R. Almeida, L. A. Herzenberg and L. A. Herzenberg. 2010. Two physically, functionally, and developmentally distinct peritoneal macrophage subsets. Proc. Natl. Acad. Sci. USA 107: 2568-2573.
23. Khan, M. A., S. Bouzari, C. Ma, C. M. Rosenberger, K. S. Bergstrom, D. L. Gibson, T. S. Steiner, and B. A. Vallance. 2008. Flagellin-dependent and -independent inflammatory responses following infection by enteropathogenic *Escherichia coli* and *Citrobacter rodentium*. Infect. Immun. 76: 1410-1422.
24. Lee, C. C., A. M. Avalos, and H. L. Ploegh. 2012. Accessory molecules for Tolllike receptors and their function. Nat. Rev. Immunol. 12: 168-179.
25. Divanovic, S., A. Trompette, S. F. Atabani, R. Madan, D. T. Golenbock, A. Visintin, R. W. Finberg, A. Tarakhovsky, S. N. Vogel, Y. Belkaid, et al. 2005. Inhibition of TLR-4/MD-2 signaling by RP105/MD-1. J. Endotoxin Res. 11: 363-368.
26. Ip, W. K., K. Takahashi, K. J. Moore, L. M. Stuart, and R. A. Ezekowitz. 2008. Mannose-binding lectin enhances Toll-like receptors 2 and 6 signaling from the phagosome. J. Exp. Med. 205: 169-181.
27. Fanning, S., L. J. Hall, M. Cronin, A. Zomer, J. MacSharry, D. Goulding, M. O. Motherway, F. Shanahan, K. Nally, G. Dougan, and D. van Sinderen. 2012. Bifidobacterial surface-exopolysaccharide facilitates commensal-host interaction through immune modulation and pathogen protection. Proc. Natl. Acad. Sci. USA 109: 2108-2113.
28. Mazmanian, S. K., and D. L. Kasper. 2006. The love-hate relationship between bacterial polysaccharides and the host immune system. Nat. Rev. Immunol. 6:849-858.
29. Kalka-Moll, W. M., A. O. Tzianabos, P. W. Bryant, M. Niemeyer, H. L. Ploegh, and D. L. Kasper. 2002. Zwitterionic polysaccharides stimulate T cells by MHC class II dependent interactions. J. Immunol. 169: 6149-6153.
30. Fraga-Silva, T. F., J. Venturini, and M. S. de Arruda. 2013. Trafficking of phagocytic peritoneal cells in hypoinsulinemic-hyperglycemic mice with systemic candidiasis. BMC Infect. Dis. 13: 147.
31. An, D., C. Na, J. Bielawski, Y. A. Hannun, and D. L. Kasper. 2011. Membrane sphingolipids as essential molecular signals for *Bacteroides* survival in the intestine. Proc. Natl. Acad. Sci. USA 108(Suppl 1): 4666-4671.
32. Bouladoux, N., J. A. Hall, J. R. Grainger, L. M. dos Santos, M. G. Kann, V. Nagarajan, D. Verthelyi, and Y. Belkaid. 2012. Regulatory role of suppressive motifs from commensal DNA. Mucosal Immunol. 5: 623-634.
33. Lebeer, S., J. Vanderleyden, and S. C. De Keersmaecker. 2008. Genes and molecules of lactobacilli supporting probiotic action. Microbiol. Mol. Biol. Rev 72: 728-764 (Table of Contents.).

Example 2

EPS Pretreatment Protects Subjects from Multiple Sclerosis (MS)

This was demonstrated by administration of the EPS to mice. In particular, a murine model for multiple sclerosis known as EAE (Experimental autoimmune encephalomyelitis (EAE) is the most commonly used experimental model for the human inflammatory demyelinating disease, multiple sclerosis (MS)).

Figure 8:
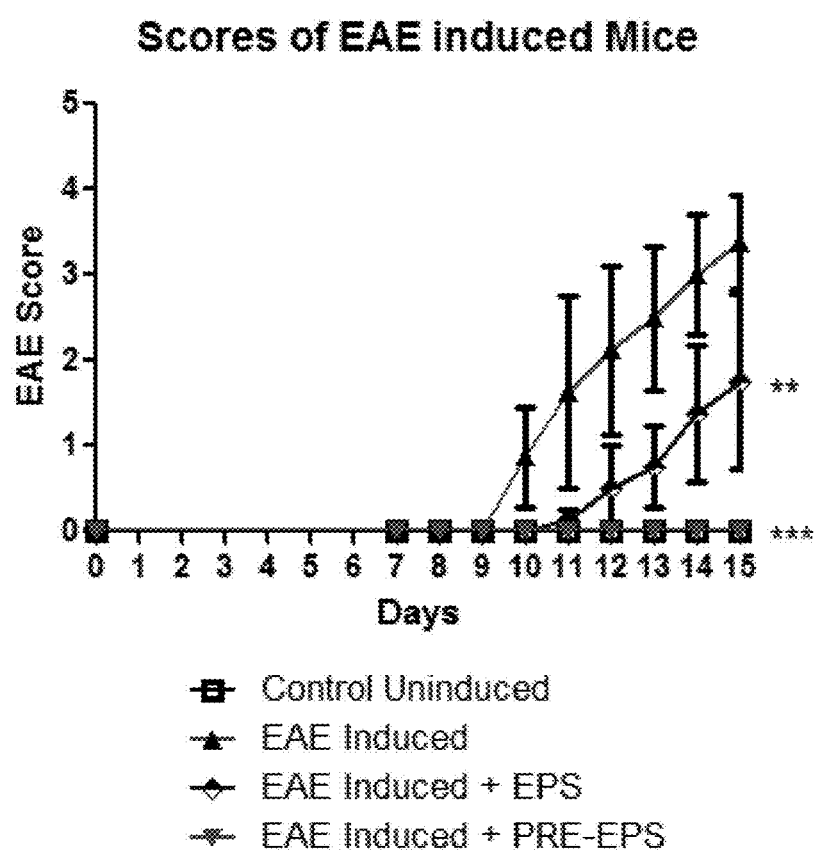
FIG. 8 depicts scores of EAE in induced mice. Filled triangles were EAE induced, open triangles were treated with EPS at the time of EAE induction and every three days following and downward pointed triangles were pretreated with EPS 3 days prior to EAE induction and every three days following.

200 ug of EPS (described in Example 1) was administered per 20 g of mouse every three days for the course of the experiment. Controls were injected with PBS. With regards to FIG. 8, filled triangles were EAE induced, open triangles were treated with EPS at the time of EAE induction and every three days following and downward point triangles were pretreated with EPS 3 days prior to EAE induction and every three days following.

Subjects that received EPS prior to induction of disease were protected from the disease, while subjects that received EPS at the time of disease induction displayed partial protection. Thus, EPS finds use in preventing MS and treating recurrent relapses in MS.

BIBLIOGRAPHY

U.S. Pat. No. 8,357,794

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A method to treat an autoimmune disease comprising administering to a subject in need thereof an effective amount of a composition consisting essentially of purified bacterial exopoly saccharide (EPS) so as to treat said autoimmune disease, wherein the EPS is obtained from *Bacillus subtilis*, wherein the autoimmune disease is multiple sclerosis (MS).

2. The method of claim 1, wherein the EPS inhibited, reduced the number or severity of recurrent relapses in M S.

3. A method to treat an inflammatory disease comprising administering to a human subject in need thereof an effective amount of a composition consisting essentially of purified bacterial exopoly saccharide (EPS) so as to treat said inflammatory disease, wherein the EPS is obtained from *Bacillus subtilis*, wherein the inflammatory disease is inflammatory bowel disease.

4. A method to prevent or treat ulcerative colitis comprising administering to a human subject in need thereof an effective amount of a composition consisting essentially of purified bacterial exopolysaccharide (EPS) so as to prevent or treat said ulcerative colitis, wherein the EPS is obtained from *Bacillus subtilis*.

5. A method to prevent or treat multiple sclerosis comprising administering to a subject in need thereof an effective amount of a composition consisting essentially of purified bacterial exopolysaccharide (EPS) so as to prevent or treat said multiple sclerosis, wherein the EPS is obtained from *Bacillus subtilis*.

6. A method to treat graft vs. host disease comprising administering to a subject in need thereof an effective amount of a composition consisting essentially of purified bacterial exopolysaccharide (EPS) so as to treat said graft vs. host disease, wherein the EPS is obtained from *Bacillus subtilis*.

* * * * *

UNITED STATES PATENT AND TRADEMARK OFFICE
CERTIFICATE OF CORRECTION

Page 1 of 1

PATENT NO. : 10,383,888 B2
APPLICATION NO. : 15/095604
DATED : August 20, 2019
INVENTOR(S) : Osborne et al.

It is certified that error appears in the above-identified patent and that said Letters Patent is hereby corrected as shown below:

On the Title Page

In Column 2, item (56) under "Other Publications", Line 28, delete "a" and insert --A-- therefor In Column 2, item (56) under "Other Publications", Line 38, delete "rodentiunn-induced" and insert --rodentium-induced-- therefor In the Claims In Column 22, Line 47, in Claim 1, delete "exopoly saccharide" and insert --exopolysaccharide-- therefor In Column 22, Line 56, in Claim 3, delete "exopoly saccharide" and insert --exopolysaccharide-- therefor Signed and Sealed this
Fourteenth Day of April, 2020

Andrei Iancu
*Director of the United States Patent and Trademark Office*